United States Patent
Zweig et al.

(10) Patent No.: US 7,072,035 B2
(45) Date of Patent: Jul. 4, 2006

(54) VERIFICATION DEVICE FOR OPTICAL CLINICAL ASSAY SYSTEMS

(75) Inventors: Stephen E. Zweig, Los Gatos, CA (US); Benjamin G. Meyer, Saratoga, CA (US); Thomas D. Downey, Cupertino, CA (US)

(73) Assignee: Beckman Coulter, Fullerton, CA (US)

( * ) Notice: Subject to any disclaimer, the term of this patent is extended or adjusted under 35 U.S.C. 154(b) by 0 days.

(21) Appl. No.: 11/089,279

(22) Filed: Mar. 23, 2005

(65) Prior Publication Data

US 2005/0206875 A1    Sep. 22, 2005

Related U.S. Application Data

(63) Continuation of application No. 10/770,786, filed on Feb. 2, 2004, now abandoned, which is a continuation of application No. 09/564,390, filed on May 1, 2000, now abandoned, which is a continuation of application No. 09/138,824, filed on Aug. 24, 1998, now Pat. No. 6,061,128.

(60) Provisional application No. 60/057,903, filed on Sep. 4, 1997.

(51) Int. Cl.
*G01J 1/10* (2006.01)
*G01N 21/55* (2006.01)

(52) U.S. Cl. ............... 356/243.4; 356/243.5; 356/448; 250/252.1; 422/82.05

(58) Field of Classification Search ............ 356/243.1, 356/243.4, 243.5; 250/252.1; 422/57–58, 422/67–68, 82.05; 436/46, 48
See application file for complete search history.

(56) References Cited

U.S. PATENT DOCUMENTS

| | | | |
|---|---|---|---|
| 4,031,529 A | 6/1977 | Borel et al. | |
| 4,454,752 A | 6/1984 | Scordato | |
| 4,509,959 A | 4/1985 | McCombs | |
| 4,523,852 A | 6/1985 | Bauer | |
| 4,729,657 A | 3/1988 | Cooper et al. | |
| 4,849,340 A | 7/1989 | Oberhardt | |
| 4,948,961 A | 8/1990 | Hillman et al. | |
| 5,030,005 A | 7/1991 | Swope et al. | |
| 5,151,755 A | 9/1992 | Seto | |
| 5,204,525 A | 4/1993 | Hillman et al. | |
| 5,284,770 A | 2/1994 | Adrian et al. | |
| 5,348,005 A | 9/1994 | Merrick et al. | |
| 5,416,575 A | 5/1995 | Schwartz et al. | |
| 5,418,143 A | 5/1995 | Zweig | |
| 5,504,011 A | 4/1996 | Gavin et al. | |
| 5,591,403 A | 1/1997 | Gavin et al. | |
| 5,592,290 A | 1/1997 | Arai et al. | |
| 6,061,128 A | 5/2000 | Zweig et al. | |
| 6,628,389 B1 * | 9/2003 | Akada et al. | ............... 356/364 |
| 6,927,853 B1 * | 8/2005 | Geiler et al. | ............... 356/367 |

\* cited by examiner

*Primary Examiner*—Layla G. Lauchman
(74) *Attorney, Agent, or Firm*—Townsend & Townsend & Crew LLP

(57) ABSTRACT

A device and method for verifying correct performance of an optical clinical assay system is provided.

7 Claims, 2 Drawing Sheets

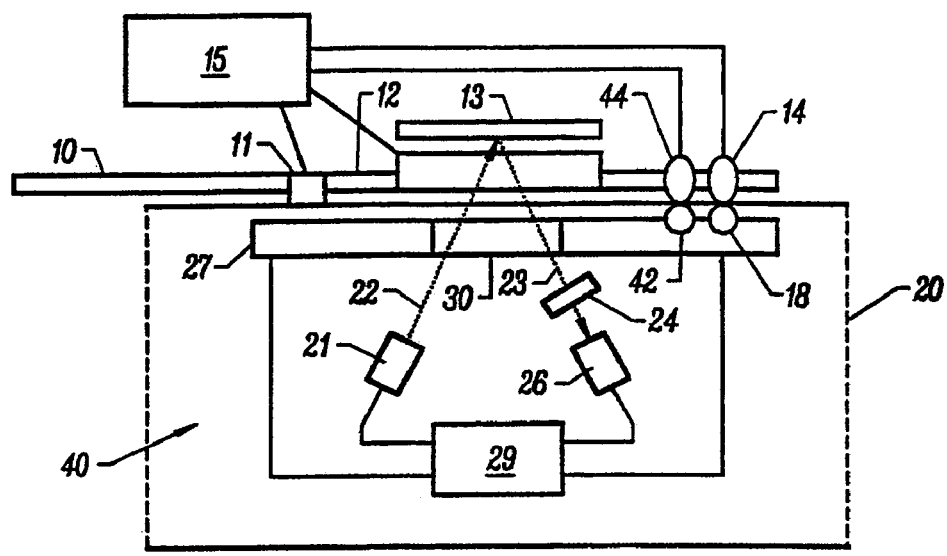
FIG. 1
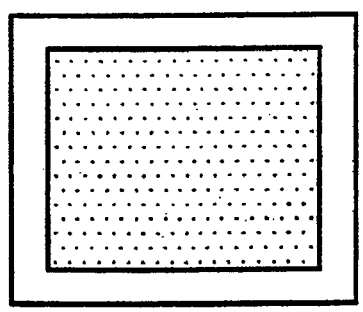    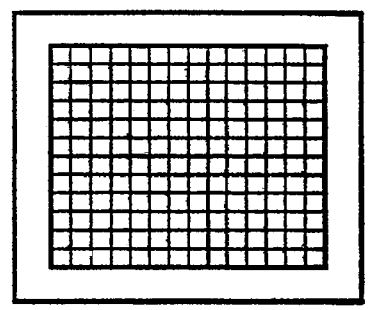
FIG. 2A          FIG. 2B

VERIFICATION DEVICE FOR OPTICAL CLINICAL ASSAY SYSTEMS

This application is a continuation of application Ser. No. 10/770,786, filed Feb. 2, 2004, now abandoned, which is a continuation of application Ser. No. 09/564,390, filed May 1, 2000, now abandoned, which is a continuation of application Ser. No. 09/138,824, filed Aug. 24, 1998, now U.S. Pat. No. 6,061,128, which claims the benefit of Provisional Application No. 60/057,903, filed Sep. 4, 1997.

BACKGROUND OF THE INVENTION

Increasingly in modern clinical chemistry, whole blood samples, often obtained by finger stick methods, are analyzed using automated automatic analysis systems (meters) which employ disposable (often one-time use) test elements, and a non-disposable electronic test device that analyzes the reaction occurring in the whole blood sample in the disposable test element, and then outputs an answer. Such systems are used for analyzing whole blood samples for glucose, cholesterol, and increasingly, more complex tests such as coagulation testing (prothrombin time, activated partial thromboplastin time), enzymatic analytes, and the like.

Because the answer from these devices are often used to make a clinical decision that can significantly impact the health and well-being of a patient, verification methods to insure that the analytical devices are performing correctly are of obvious importance.

One common method for verifying correct performance of a clinical analytical system is through the use of control solution, which is usually a liquid chemical solution with known reactivity. If the analytical device gives the correct answer with a known reference chemical, then the overall performance of the system can be assessed.

With modern one-shot, disposable test elements, however, the problem with liquid control testing is that it is destructive. The disposable test element has been destroyed as a result of the testing, and only the now-validated meter now survives to test the actual sample. For this reason, modern verification methods tend to shift validation of disposable test elements to manufacturers, who validate batches of disposable test elements by statistical sampling methods. The problem of meter verification remains, however. Meters are typically used for years, and can be exposed to environmental extremes, misuse, and mechanical shock.

Because meter verification using liquid control devices and disposable test units is an expensive process, and because test unit verification is inherently best suited to statistical lot testing by the manufacturer, there is a need for low-cost methods that can verify the performance of the meter without the use of liquid control solution and disposable test units.

Analytical devices for temperature sensitive enzymatic analytes, such as blood coagulation, typically have a temperature controlled reaction stage, means to determine the start of the enzymatic reaction, optical means to access the progress of the reaction, and computational means (typically a microprocessor or microcontroller) to interpret the progress of the reaction and output an answer. To completely verify the performance of the analysis system, each subsystem must be assessed. The temperature controlled reaction stage must be tested for proper temperature control, the means to determine the start of the enzymatic reaction must be tested for proper sensitivity, the optical means to access reaction progress must be tested (light source, light detector, integrity of optical stage, etc.), and finally the computational means must be tested. Alternatively partial verification of some of the subsystems may be done, and the remainder of the subsystems tested by alternate means, such as liquid control solution and a disposable test unit.

To verify the function of such analytical devices, electronic verification or "control" devices or circuits are commonly used. Such verification devices can simulate the action of an enzymatic sample interacting with a disposable. reagent. If the analytical device returns the proper answer after analysis of the verification device, then the proper functioning of the analytical device can be verified without the expense of using the one time use reagent cartridges.

The use of reference paint chips to calibrate and verify photometric devices has long been known in the art. When applied to home blood glucose monitors, such reference chips are often referred to as "check strip". For example, the LifeScan One-Touch™ blood glucose monitor includes a colorimetric "check strip" in with its meter system. This "check strip" consists of an opaque plastic strip with a paint chip of known colorimetric properties affixed to it. The check strip is inserted into the meter, and is used to verify the performance of the meter's colorimetric photodetector. The system does not vary the intensity of the colorimetric paint chip target as a function of time to simulate a normal test reaction, nor does it incorporate means to monitor the analytical devices' temperature.

Recent refinements to the basic "paint chip" technique, suitable for clinical reagents and instrumentation, include U.S. Pat. Nos. 4,509,959; 4,523,852; 4,729,657; 5,151,755; 5,284,770; and 5,592,290. U.S. Pat. No. 4,509,959 disclosed an apparatus incorporating many such reference color chips. U.S. Pat. No. 4,523,852 disclosed a reference standard, suitable for visually read diagnostic reagent test strips, consisting of many colored reference areas of differing hues. U.S. Pat. No. 4,729,657 disclosed photometer calibration methods using two or more reflectance standards and using least squares regression line analysis to construct and store calibration curves in the analytical device's memory. U.S. Pat. No. 5,151,755 disclosed methods to detect defects in biochemical analysis apparatuses measurement means by irradiating a reference density plate with light that has passed through a plurality of interference filters and comparing the relative amounts of reflected light obtained by these different measurements. U.S. Pat. No. 5,284,770 disclosed use of a check strip, along with an analytical instrument having a user insertable key (memory chip) containing the parameters of acceptable check strip performance, so that correct instrument performance can be automatically verified. U.S. Pat. No. 5,592,290 disclosed optical analyzer instrument error correction methods using standard color plates incorporating dyes with absorption spectrum similar to the analytical reagent normally read by the analyzer. These standard color plates are then used in conjunction with a second reference optical analyzer and a specific correction algorithm to correct the instrument error in the first instrument.

In addition to passive "paint chip" verification methods, a number of different active (typically electronic) verification methods have also been used. These active verification methods typically involve electronic components, and often produce a dynamic (as opposed to a static) reference signal to the analytical instrument.

U.S. Pat No. 4,454,752 disclosed a test circuit for use in a photometric coagulation instrument for plasma samples that verified the electronic circuitry of the instrument, wherein the rapid rise in clot density of a plasma sample may be simulated by a applying to the clot detection circuitry of the instrument a synthetic waveform that simulates the signal that results during clot formation in a reagent plasma mixture. However, this patent did not disclose methods by which the proper functioning of an instrument capable of measuring whole blood can be analyzed. The disclosed methods are capable of verifying only that the clot detection circuits of an photometric plasma coagulation instrument are performing properly. The patent did not disclose methods by which other instrument functions such as temperature control, absence of optical system light leaks, proper detection of sample insertion, etc., may also be verified.

Verification methods suitable for partially verifying the function of certain whole blood coagulation analyzers and unitized reagent cartridges are also known in the art. For example, U.S. Pat. Nos. 4,948,961 and 5,204,525 disclosed a quality control device for an instrument with an analysis cartridge constructed so that the instrument's light passes through the cartridge's internal chamber. Such systems have been used for a number of whole blood clinical tests, including whole blood prothrombin time assays when the internal chamber is filled with thromboplastin, and the cessation of red cell movement is tracked by light scattering techniques.

U.S. Pat. No. 5,204,525 disclosed a control device using a liquid crystal cell interposed between the light source and detector in an analytical instrument, and a polarizing filter, so that the passage or block passage of light between the analytical device's light source and light detector when the voltage to the liquid crystal is modulated. However, neither U.S. Pat. No. 5,204,525 nor U.S. Pat. No. 4,948,961 disclosed means by which the temperature control of an analytical device may be verified. Although these publications disclosed devices useful for monitoring the function of optically transmissive reaction chambers in which the light source passes through the chamber, and which the reaction in question does not alter the wavelength of the light emitted by the instrument's light source, they did not disclose devices useful for monitoring the function of fluorescent test strip articles such as those disclosed in U.S. Pat. No. 5,418,143. In such systems, light of one wavelength enters a test strip, and excites a fluorescent compound which then emits light that exits the test strip at the same side as the light source (rather than passing through a reaction chamber), and at a different wavelength.

Another type of control device is found in the Boehringer Mannheim "Coaguchek" whole blood prothrombin time analysis device disclosed by U.S. Pat. No. 4,849,340. This device uses a disposable reagent cartridge consisting of a chamber with thromboplastin and magnetic particles. The disposable reagent cartridge is placed in a stage in the analysis device, and a blood sample is added. The analysis device subjects the reagent cartridge to a varying magnetic field, and detects the motion of the magnetic particles by the optical interaction between the motion of the magnetic particles and a beam of light. In normal operation, when blood is applied to the disposable reagent cartridge, the magnetic particles are free to move in suspension, and thus provide a high degree of modulation to the optical signal in response to the varying magnetic field. As the blood clots in response to the thromboplastin reagent, the magnetic particles become less able to move, and thus provide a progressively smaller amount of modulation to the optical signal as time progresses.

An "electronic control" is provided for the Coaguchek. (Boehringer Mannheim electronic control user manual, 1996). This "electronic control" consists of a separate device consisting of a disposable reagent sized probe that fits in to the reagent stage on the Coaguchek device. The probe contains a magnetic coil pickup, a light emitting diode, and means to vary the intensity of the response of the light emitting diode to current generated by the magnetic coil pickup. By using this "electronic control" device, the operator can verify that the varying magnetic field generator on the Coaguchek is operating properly, and that the optical sensor on the Coaguchek is also operating properly. The temperature of the reaction stage, and the performance of the optical light source on the Coaguchek, are not tested by this device, however.

In addition to passive (time unvarying reference signal) and active (time varying reference signal) verification devices, a third type of verification methodology has been disclosed which incorporates certain verification systems on to the disposable reagent itself. This is disclosed by in U.S. Pat. Nos. 5,591,403 and 5,504,011. U.S. Pat. No. 5,591,403 disclosed a reaction chamber cuvette, useful for prothrombin time testing, with multiple conduits. One or more conduits contain the reaction chemistry for the prothrombin time reaction itself, and other conduits contain control agents useful for assessing certain functions of the analytical instrument that reads the test cartridge, and the test cartridge itself. Typically one "control" conduit will contain a vitamin K dependent clotting factor concentrate, and a different "control" conduit will contain an anticoagulant. In a properly functioning instrument, the control conduit with the vitamin K dependent clotting factor concentrate will initiate a coagulation signal early, and the control conduit with the, anticoagulant will initiate a coagulation signal late. This tests the proper function of those meter detector elements that read the status of the control conduits. Because the control elements are incorporated into normal prothrombin time reaction cuvette, an independent, non-destructive, test of proper meter function is not possible with this system.

Thus, a need exists for an improved verification device. This need and others are addressed by the instant invention.

SUMMARY OF THE INVENTION

One aspect of the invention is a method for verifying the output of a system having a radiation source and a radiation detector, said method comprising positioning a reference surface to receive radiation from the radiation source and return radiation to the detector; and modulating at least one of the radiation from the source and the radiation to the detector over time to emulate reflective or radiation characteristics of a chemical or biological reaction on the reference surface.

A further aspect of the invention is a method for verifying the output of a system having a radiation source and a radiation detector, said method comprising positioning a reference surface to receive radiation from the radiation source and return radiation to the detector; and modulating at least one of the radiation from the source and the radiation to the detector over time in response to temperature changes. In some embodiments, the temperature changes are determined within the system. In further embodiments, the temperature changes are determined external to the system.

A further aspect of the invention is an apparatus for use in combination with an analyzer having a radiation source and a radiation detector, said apparatus comprising a reference surface which produces return radiation in response to receiving radiation from the source, and means disposed adjacent the radiation surface for modulating at least one of radiation to the reference surface or radiation from the reference surface. In some embodiments the modulating means modulates the radiation over time to emulate reflective or radiation characteristics of a chemical or biological reaction on the reference surface. In further embodiments the modulation means modulates the radiation in response to changes in temperature.

A further aspect of the invention is an electronically controlled optical reference device useful for the verification of a clinical analytical system having an optical detection apparatus, the reference device comprising, an opaque optical reference; an optical shutter; means for controlling the percent exposure of the optical reference to the optical detection apparatus; optionally, a means to monitor the temperature of a reaction stage of the clinical analytical system; and an algorithm or method that controls the rate at which the optical reference is selectively revealed to the optical detection apparatus; said algorithm or method being selected as to simulate the reaction rates of one or more levels of clinical analytes reacting with a test reagent.

A further aspect of the invention is a verification device useful for determining the proper function of an optical, temperature controlled analytical instrument, the device comprising an electronic optical shutter with an optically active backing, interposed between an optical signal emitted by the analytical instrument and an optical detector mounted on the analytical instrument; a temperature sensor, the sensor contacting a reaction stage on the analytical instrument; and verification device electrodes, the verification device electrodes making contact with electrodes on the reaction stage of the analytical instrument; wherein the action of the device is initiated by a resistance drop across the verification device electrodes, and wherein the optical transmission of the liquid crystal shutter is modulated as a function of time and of the temperature of the reaction stage, wherein a range of levels of enzymatic activity measured by the analytical instrument at various operating temperatures is simulated.

A further aspect of the invention is a verification device useful for determining the proper function of an optical, temperature controlled analytical instrument, the device comprising an optical shutter-fluorescent backing assembly comprising an optical shutter having a fluorescent backing placed on one side of the optical shutter; the assembly being interposed between an optical signal emitted by the analytical instrument and an optical detector mounted on the analytical instrument; a thermocouple in contact with a reaction stage on the analytical instrument; and verification device electrodes, the verification device electrodes making contact with electrodes on the reaction stage of the analytical instrument; wherein the action of the device is initiated by a resistance drop across the device electrode, and wherein the fluorescence of the optical shutter-fluorescent backing assembly is modulated as a function of time and of the temperature of the reaction stage, wherein a range of levels of enzymatic activity measured by the analytical instrument at various operating temperatures is simulated.

A further aspect of the invention is an electronically controlled optical reference device, useful for the verification of an analytical instrument having an optical detection apparatus and using optically read reagent test strips, the device comprising an opaque optical reference, which simulates the optical characteristics of a reagent test strip after reaction with its intended clinical sample; an optical shutter; a means for controlling the percent exposure of the optical reference to the optical detection apparatus; and an algorithm or method that controls the rate at which the check strip is selectively revealed to the optical detection apparatus, said algorithm or method being selected as to mimic the reaction rates of one or more levels of clinical analytes reacting with a reagent test strip.

A further aspect of the invention is a method for verifying the correct performance of a clinical analytical system comprising an optical detection apparatus, the method comprising contacting the clinical analytical system with an electronically controlled optical reference device useful for the verification of clinical devices using optically read reagent test strips, the reference device comprising, an opaque optical reference, which simulates the optical characteristics of a reagent test strip after reaction with its intended clinical sample; an optical shutter; means for controlling the percent exposure of the optical reference to the optical detection apparatus; optionally, a means to monitor the temperature of the clinical analytical system; and an algorithm or method that controls the rate at which the optical reference is selectively revealed to the optical device, said algorithm or method being selected so as to mimic the reaction rates of one or more levels of clinical analytes reacting with a reagent test strip; and analyzing the optical reference; wherein an expected result of analysis of the optical reference by the clinical analytical system is predictive of the correct performance of the clinical analytical system.

A further aspect of the invention is a method for verifying the temperature control of a clinical analytical system comprising an optical detection apparatus, the method comprising contacting the clinical analytical system with a verification device useful for determining the proper function of an optical, temperature controlled analytical instrument, the device comprising an electronic optical shutter with an optically active backing, interposed between an optical signal emitted by the analytical instrument and an optical detector mounted on the enzymatic analytical instrument; a temperature sensor, the sensor contacting a reaction chamber on the analytical instrument; and verification device electrodes, the verification device electrodes making contact with electrodes on the reaction chamber of the analytical instrument; wherein the action of the device is initiated by a resistance drop across the verification device electrodes, and wherein the optical transmission of the liquid crystal shutter is modulated as a function of time and of the temperature of the reaction chamber, wherein a range of levels of enzymatic activity measured by the analytical instrument at a range of operating temperatures is simulated, and analyzing the optical reference; wherein an expected result of analysis of the optical reference by the clinical analytical system is predictive of the correct operating temperature of the reaction chamber of the clinical analytical system.

BRIEF DESCRIPTION OF THE DRAWINGS

FIG. 1 is a diagram depicting an electronic strip, emulator constructed according to the principles of this disclosure (outside the dotted box), interacting with an exemplary test device (inside the dotted box).

FIGS. 2A and 2B depict two types of optical shutters. The shutter in FIG. 2A comprises a single shutter element, which can be gradually varied from non-transmissive is to transmissive. The optical shutter in FIG. 2B comprises numerous shutter "pixel" elements.

DESCRIPTION OF THE PREFERRED EMBODIMENT

Figure 3:
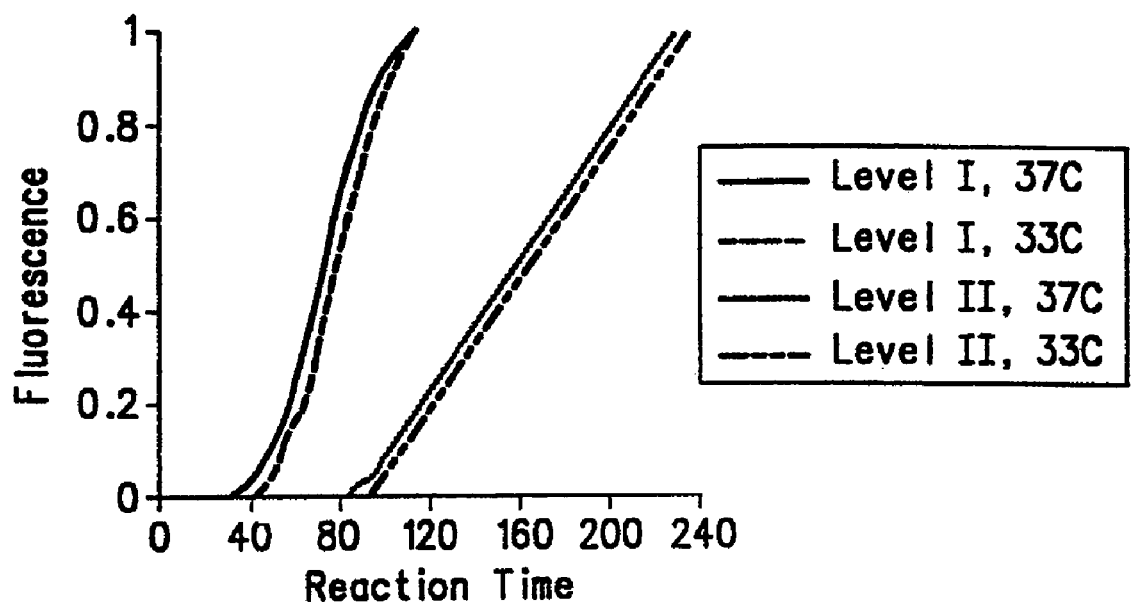
FIG. 3 is a graph depicting the output from the electronic verification device when the analytical device (meter) is at a normal temperature (37° C.), and at an aberrant temperature (33° C.). Here, Level I mimics a prothrombin time reaction curve obtained from a test sample with a normal prothrombin time value, and Level II mimics the prothrombin time reaction curve obtained from a test sample with an elevated prothrombin time value.

The present invention provides a method for verifying the output of a system having a radiation source and a radiation detector, said method comprising positioning a reference surface to receive radiation from the radiation source and return radiation to the detector; and modulating at least one of the radiation from the source and the radiation to the detector over time to emulate reflective or radiation characteristics of a chemical or biological reaction on the reference surface. In some aspects of the invention, the modulator may operate without the reference surface by selectively reflecting light.

The present invention also provides a method for verifying the output of a system having a radiation source and a radiation detector, said method comprising positioning a reference surface to receive radiation from the radiation source and return radiation to the detector; and modulating at least one of the radiation from the source and the radiation to the detector over time in response to temperature changes. In some embodiments, the temperature changes are determined within the system. In further embodiments, the temperature changes are determined external to the system.

The present invention also provides an apparatus for use in combination with an analyzer having a radiation source and a radiation detector, said apparatus comprising a reference surface which produces return radiation in response to receiving radiation from the source, and means disposed adjacent the radiation surface for modulating at least one of radiation to the reference surface or radiation from the reference surface. In some embodiments the modulating means modulates the radiation over time to emulate reflective or radiation characteristics of a chemical or biological reaction on the reference surface. In further embodiments the modulation means modulates the radiation in response to changes in temperature.

The present invention also provides a verification device for a clinical analytical system or instrument. Such a device is also referred to herein as a test strip emulator, a control test simulator, and an electronically controlled optical reference device. The verification device is typically an electronically controlled optical reference device useful for the verification of a clinical analytical system having an optical detection apparatus. The reference device comprised an opaque optical reference or "target", an optical shutter, and means for controlling the percent exposure of the optical reference to the optical detection apparatus. The opaque optical reference preferably simulates a colorimetric, fluorescent, or luminescent reagent test strip. Optionally, a means to monitor the temperature of a reaction stage of the clinical analytical system is included as part of the device. The device is preferably programed with an algorithm or comprises a method that controls the rate at which the optical reference is selectively revealed to the optical detection apparatus. Typically the selective revealing of the optical reference is done by exposing the optical reference to the optical detection apparatus over a specified time interval. The algorithm or method is selected so as to simulate the reaction rates of one or more levels of clinical analytes reacting with a test reagent. The algorithm or method can be modified to account for the temperature of a reaction stage or chamber in the analytical system.

In some embodiments of the invention, the device of comprises one or more first electrodes, wherein electrodes contact one or more second electrodes on a reaction stage of the clinical analytical system. The electrical resistance across the electrodes in the reference device is modulated to simulate the addition or removal of a disposable reagent test strip or cartridge or a liquid sample to the clinical analytical system.

The optical shutter of the device may be electronically operated. Exemplary shutters include but are not limited to a liquid crystal shutter, a magneto-optical shutter, a Faraday effect optical shutter, a thermochromic optical shutter, an electrochromic optical shutter, or a micro-mechanical optical shutter. The optical shutter may be divided into a plurality of independently or semi-independently controlled pixel elements, such that the optical shutter modulates the intensity of an optical signal by varying the optical state of the shutter pixels in a time dependent manner.

In some embodiments, the optical shutter comprises a fluorescent backing on one side of the optical shutter, and a first optical signal of a first wavelength passes through the optical shutter and interacts with the fluorescence backing, and a fluorescence signal of a second wavelength passes back through the optical shutter. In further embodiments, the optical shutter comprises a colored backing on one side of the optical shutter, and a first optical signal consisting of a first spectrum of wavelengths passes through the optical shutter and interacts with the colored backing, and a second optical signal consisting of a subset of the first spectrum of wavelengths passes back through the optical shutter. The optical shutter may also comprise a luminescent backing on one side of the optical shutter, with the optical signal comprising a time increasing or time decreasing luminescence signal.

In a further feature of the invention, a thermocouple monitors the temperature of the reaction stage of the analytical device. The transparency of the optical shutter may be modulated as a function of time and of a thermocouple monitored temperature of the reaction stage, wherein a range of levels of enzymatic activity measured by the analytical system at various operating temperatures is simulated.

In some embodiments of the invention, the verification device provides a means to monitor a reagent present and/or blood present sensor on the clinical analytical device, wherein a stimulus to these sensors is provided to signal readiness of the meter for testing a clinical sample.

The instant invention also provides a verification device useful for determining the proper function of an optical, temperature controlled analytical instrument. Typically such a device will comprise an electronic optical shutter with an optically active backing, interposed between an optical signal emitted by the analytical instrument and an optical detector mounted on the analytical instrument; a temperature sensor, the sensor contacting a reaction stage on the analytical instrument; and verification device electrodes, the verification device electrodes making contact with electrodes on the reaction stage of the analytical instrument. The action of the device is preferably initiated by a resistance drop across the verification device electrodes. The optical transmission of the liquid crystal shutter is modulated as a function of time and of the temperature of the reaction stage, wherein a range of levels of enzymatic activity measured by the analytical instrument at various operating temperatures is simulated. The reaction stage of the analytical device may be heated.

In some embodiments the device comprises an optical shutter-fluorescent backing assembly comprising an optical shutter having a fluorescent backing placed on one side of the optical shutter; the assembly being interposed between an optical signal emitted by the analytical instrument and an optical detector mounted on the analytical instrument; a thermocouple in contact with a reaction stage on the analytical instrument; and verification device electrodes, the verification device electrodes making contact with electrodes on the reaction stage of the analytical instrument. The action of the device is initiated by a resistance drop across the device electrode. The fluorescence of the optical shutter-fluorescent backing assembly is modulated as a function of time and of the temperature of the reaction stage, wherein a range of levels of enzymatic activity measured by the analytical instrument at various operating temperatures is simulated. The reaction stage of the analytical device may be heated.

The instant invention also provides an electronically controlled optical reference device, useful for the verification of an analytical instrument having an optical detection apparatus and using optically read reagent test strips. The device comprises an opaque optical reference, which simulates the optical characteristics of a reagent test strip after reaction with its intended clinical sample; an optical shutter; a means for controlling the percent exposure of the optical reference to the optical detection apparatus, and an algorithm or method that controls the rate at which the check strip is selectively revealed to the optical detection apparatus, said algorithm or method being selected as to mimic the reaction rates of one or more levels of clinical analytes reacting with a reagent test strip. In a preferred embodiment, the reagent is thromboplastin.

The instant invention also provides a method for verifying the correct performance of a clinical analytical system comprising an optical detection apparatus using the devices of the instant invention. In a preferred embodiment, the clinical analytical system is contacted with an electronically controlled optical reference device useful for the verification of clinical devices using optically read reagent test strips. The reference device, for example, comprises an opaque optical reference, which simulates the optical characteristics of a reagent test strip after reaction with its intended clinical sample; an optical shutter; means for controlling the percent exposure of the optical reference to the optical detection apparatus; optionally, a means to monitor the temperature of the clinical analytical system; and an algorithm or method that controls the rate at which the optical reference is selectively revealed to the optical device, said algorithm or method being selected as to mimic the reaction rates of one or more levels of clinical analytes reacting with a reagent test strip. An expected result of analysis of the optical reference by the clinical analytical system is predictive of the correct performance of the clinical analytical system.

The instant invention also provides a method for verifying the temperature control of a clinical analytical system comprising an optical detection apparatus using the devices of the instant invention. In a preferred embodiment, the method comprises contacting the clinical analytical system with a verification device useful for determining the proper function of an optical, temperature controlled analytical instrument. For example, the device comprises an electronic optical shutter with an optically active backing, interposed between an optical signal emitted by the analytical instrument and an optical detector mounted on the enzymatic analytical instrument; a temperature sensor, the sensor contacting a reaction chamber on the analytical instrument; and verification device electrodes, the verification device electrodes making contact with electrodes on the reaction chamber of the analytical instrument. The action of the device is initiated by a resistance drop across the verification device electrodes, and wherein the optical transmission of the liquid crystal shutter is modulated as a function of time and of the temperature of the reaction chamber, wherein a range of levels of enzymatic activity measured by the analytical instrument at a range of operating temperatures is simulated. An expected result of analysis of the optical reference by the clinical analytical system is predictive of the correct operating temperature of the reaction chamber of the clinical analytical system.

The verification device of the invention can be provided as a probe, suitable for insertion into the reaction chamber of a colorimetric, fluorescent, or chemiluminescent test analytical instrument, with an opaque colorimetric, fluorescent or luminescent target. The reflectance, fluorescence or luminescence of the target is modulated by an optical shutter. Typically the probe will additionally contain a temperature sensor, a clock, and means to modulate the optical exposure of the probes target area according to a preset algorithm. The preset algorithm is designed to mimic the response of a normal reagent with one or more levels of test analyte. The probe may optionally contain other elements designed to interact with and test other meter functional elements, such as a meters "reagent present" and "sample present" sensors.

The optical characteristics of the opaque optical target can vary depending upon the analytical device in question. In one embodiment, the target is optically reflective and/or optically colored, so as to effectively change the distribution of various wavelengths or light intensity of the target as a function of the state of the optical shutter. In a further, embodiment, the target can made of a fluorescent material, so that the fluorescent intensity of the light detected by the analytical system's detector varies as a function of the state of the optical shutter. In a third embodiment, the backing can be luminescent (for example, an electronic luminescent panel), so that the luminescence seen by the analytical system's luminescence detector varies as a function of the state of the optical shutter. Although for brevity, this discussion will focus on fluorescent targets, it should be understood that the same principles would also apply to colorimetric or luminescent analytical systems as well.

A fluorescent target is typically composed of a fluorescent compound, with absorption and emission characteristics similar to that of the analytical devices normal fluorescent reagent. The compound will typically be incorporated into a rigid support matrix. This can be done by mixing the fluorescent target compound with a suitable support carrier, such as acrylic paint, epoxy, or the like. To maximize the optical signal-to-noise characteristics of the fluorescent target, sufficient quantities of fluorescent compound are added as to completely interact with the entire fluorescence optical excitation signal, rendering the target optically opaque. The fluorescent target shifts the wavelength of the excitation signal to a different wavelength, and the fluorescent signal emerges from the side of the target that is illuminated by the excitation wavelength.

Alternatively, if it is infeasible to make the target opaque using large amounts of fluorescent compound, the back of the target may painted with an opaque backing. The characteristics of this opaque backing may be selected to maximize the signal-to-noise performance of the fluorescent target. If the optical cutoff efficiency of the fluorescent detector's filters to the fluorescence excitation wavelengths is high, the opaque backing could be selected to be of a shiny reflective material. Alternatively, if the optical cutoff efficiency of the fluorescent detector's filters to the fluorescence excitation wavelengths is lower, a non-reflective (black) opaque backing may be chosen to minimize back reflections of the incoming excitation wavelengths to the fluorescence detector.

In yet another embodiment, the target may be luminescent, and used in a chemiluminescence detecting analytical device that has an optical detector, but does not contain a light source. The light source for the luminescent target may be provided by variety of conventional electrical lighting techniques.

The optical shutter may be a mechanical or electromechanical shutter, such as an iris as typically used to control exposure intensity in cameras, a series of louvers, or the like. Alternatively, the optical shutter may be an electro-optical shutter, such as a liquid crystal shutter, a magneto-optical electric shutter, Faraday effect optical shutter, thermochromic optical shutter, Electrochromic optical shutter, micromechanical optical shutter, or other such device. Some exemplary optical stutters suitable for the present invention are disclosed, for example, in U.S. Pat. Nos. 3,649,105; 4,556,289; 4,805,996; 4,818,080; 5,050,968; 5,455,083; 5,459,602; and 5,525,430.

The optical shutter may be composed of a single functional shutter element, or alternatively it may be composed of many smaller functional shutter elements, that collectively act to act to alter the optical characteristics of the shutter as a whole.

In an configuration, the shutter is mounted so that light illuminating the optical (fluorescent) target passes through the shutter. Fluorescent light re-emitted by the optical target may pass directly to the analytical device fluorescence detector, or optionally pass through the optical shutter on the way to the fluorescence detector. Alternatively, the optical shutter can be mounted to interact only with light emitted by the optical target. In still a further configuration, the optical shutter can interact with light both illuminating and emitted by the optical target.

The device may optionally contain means of monitoring the temperature of the probe near the target area, as well as means of modulating the fluorescence signal in response to the temperature of the target area. These means may be mechanical, such as a bimetallic strip mechanical temperature sensor device hooked up to a mechanical shutter, chemical, such as a temperature sensitive liquid crystal thermometer, or electronic, such as a thermistor, thermocouple, or the like. In the preferred embodiment, the temperature sensor is electronic.

The means to modulate the target's fluorescence may be mechanical, such as a clockwork mechanism, cam, or the like. The means may be controlled by analog electrical circuits, such as simple analog timers or the like, or the means may be controlled by digital electrical circuits, such as microprocessors, microcontrollers, and the like. In the case of mechanical means, the algorithm encoding the state of the target's fluorescence as a function of time is encoded into the design of the mechanical timing elements. In the case of analog electrical circuits, the algorithm is encoded by properly selected time constants, and the like. In the preferred case of digital microprocessor controllers, the algorithm is encoded by a specific program that controls fluorescence as a function of time, and optionally temperature and other variables.

To fully validate the analytical system's performance over a variety of sample ranges, the algorithm will ideally simulate the reaction occurring when samples with different relative activity react with test reagents. The algorithm may switch from simulating one test level to a different test level either in response to user input, or automatically as the test algorithm runs through a preset series of validation tests.

The verification device's probe may optionally contain one or more additional elements that interact with and validate other aspects of the proper function of the analytical system. For example, the probe may test the function of systems that determine if a cartridge has been properly inserted, or systems that determine if sufficient sample has been added. In the case of optical strip insertion or sample addition schemes, the probe may contain additional light emitting or light blocking devices designed to interact with appropriate optical detectors on the instrument. Alternatively, in the case of electronic strip insertion or sample addition schemes, such as those disclosed in U.S. Pat. Nos. 5,344,754 and 5,554,531, and in Zweig et. al., *Biomedical Instrumentation & Technology* 30: 245–256 (1996), the probe may contain one or more electrodes that interact with corresponding electrode sensors on the analytical device, and provide appropriate inputs to simulate normal activity.

The verification device may be constructed as a stand-alone, independently powered unit. This may be manually inserted or removed by the user, or inserted or removed by automated equipment. Alternatively, the verification device may be constructed as an integral part of the analytical device itself, and may share one or more elements (power supply, microprocessor time, memory, etc.) with the analytical device.

A schematic diagram of the verification device of the instant invention interacting with a meter is depicted in FIG. 1. In this embodiment, the meter 40 consists of an electrically heated support stage 27, containing an optical window 30 through which light 22 emitted from light source 21 can pass. The meter additionally contains an optional fluorescence filter 24 and a photodetector 26. In normal use, light 22 travels through the optics window 30 and illuminates a fluorescent reagent target. Fluorescent light 23 travels though filter 24 and after filtration illuminates photodetector 26. The meter is controlled by a microprocessor 29, which initiates test timing in response to inputs from strip detect and sample detection electrodes 28. The verification device circuit board additionally contains electrodes 14 that interacts with the strip detect and blood detect electrodes 28 on the meter's optics block 20. A thermocouple 11 performs an independent measurement of the temperature of the meter's heated optics block 27. The verification device has an optical shutter 12, with a backing 13, and a circuit board 10. A microcontroller 15 is also provided.

Figure 4:
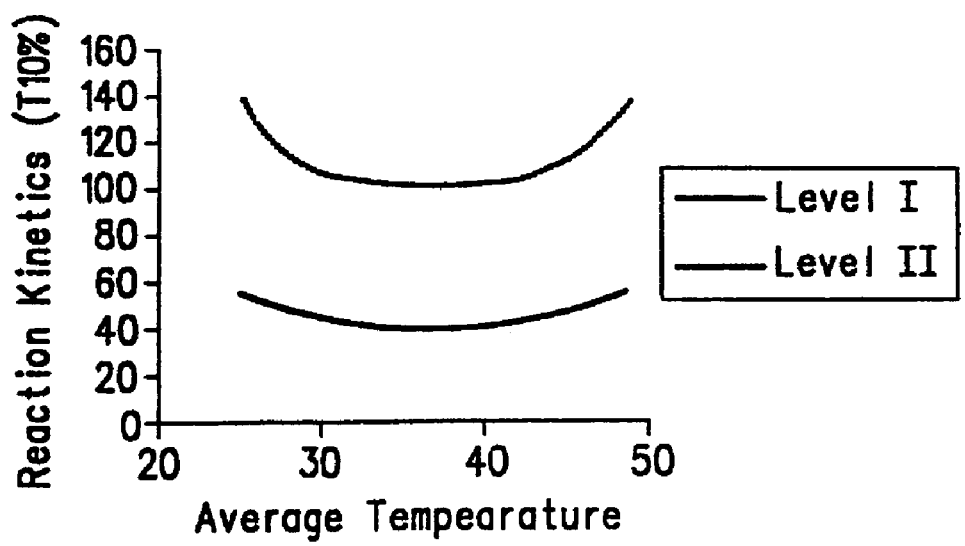
FIG. 4 depicts an example of a temperature correction algorithm altering the kinetics of fluorescence development in response to the time averaged temperature readings from the electronic verification device. The temperature algorithm is selected to match the temperature response of a real reagent test strip.

In a preferred embodiment, the verification device has an 8×8 pixel liquid crystal optical shutter 12, with an active area of 0.375×0.375", and an exterior size of 0.5"×0.6", made by Polytronics, Inc. This is placed on a 0.02" thick circuit board 10, with exterior dimensions of 0.75", and length of 2". The exterior circuit board is made to the same size as a disposable test strip unit normally used in an Avocet Medical prothrombin time detector (see Zweig, et.al., *Biomedical Instrumentation & Technoloay* 30, 245–256; FIGS. 3 and 4).

The optical shutter has a backing 13 consisting of Rhodamine 110 mixed with epoxy. The rhodamine 110 retains its normal fluorescence activity when mixed with the epoxy, and the epoxy provided a way to affix the Rhodamine 110 to the back of the optical shutter 12 in durable and permanent manner. The active elements on the circuit board are controlled by a Texas Instruments TSS400-S3 sensor signal processor 15, which is a combination microcontroller, liquid crystal display driver, and A/D converter. The TSS400 additionally contains 2K bytes of programmable EEPROM, which contained the algorithm needed to drive the system. When turned on (switches not shown), the verification device initially turns all 64 pixels of the 8×8 pixel optical shutter to the opaque mode. Electrodes 14 connecting to the strip present sensors 28 on the meter's optics block 20 are switched to conducting mode (resistance is lowered), to allow the Avocet Meter to detect that a test strip is inserted into the optics block. The meter then initiates a warm-up sequence.

In this preferred embodiment, upon reaching proper temperature, the meter then sends a signal via its sensor electrodes 28 to the verification device electrodes 14 informing the verification device that the meter is now warmed up. Alternatively, the meter can signal to the user that it is ready, and the user can manually transfer this information to the verification device by pressing an electrical switch on the verification device. After the verification device is informed that the meter is now ready to proceed, the device then reduces the resistance across a second set of electrodes 44, which interact with the blood present sensors 42 on the meter's optics block. Whereas this resistance drop is normally used to signal the application of blood to the reagent strip (see, for example, U.S. Pat. No. 5,344,754), in the instant invention it is used to signal the meter to proceed even though no blood has actually been applied.

In this preferred embodiment, the microcontroller 15 on the verification device consults an algorithm, and selectively switches an increasingly larger number of pixels on the liquid crystal shutter 12 to transparent mode as a function of a number of variables, including time, the setting of the verification device (e.g. Level I or II control, etc.), and optionally the temperature of the meter's optics stage 27 as measured by temperature sensor 11. The meter optical system 20 observes the fluorescent backing 13 through the optical shutter 12, and observes a progressive increase in overall fluorescence as a function of time. Alternatively, the verification device can progressively alter the voltage applied to a single element optical shutter element (see FIG. 2A) so as to progressively increase the transparency of the single element shutter as a function of time and temperature.

Exemplary algorithms are as follows. The verification device contains one or more stored reaction profile algorithms that control the percent light transmission of the optical shutter as a function of time. A preferred Level I algorithm is:

% fluorescence (% pixels switched on)=100*
[0.01*Reaction time−.0.35]        Equation 1:

% fluorescence (% pixels switched on)=100*
[0.02*Reaction time−0.9]          Equation 2:

% fluorescence (% pixels switched on)=100*
[0.01*Reaction time−0.05]         Equation 3:

In a preferred embodiment every ten seconds (the frequency at which the meter took data) for 240 seconds (a typical test duration) the verification device computes all three equations, and chose the results based upon the rule:

If Equation 1<0, % fluorescence=0;
If Equation 1>0 and <20%, % fluorescence=Equation 1
If Equation 1>20% and Equation 2<80%, % fluorescence=Equation 2
If Equation 2>80% and Equation 3<100%, % fluorescence=Equation 3
If Equation 3>100%, % fluorescence=100%.

This produces an "S" shaped reaction profile, shown in FIG. 3, similar to that of a normal prothrombin time (Level I) sample. In contrast, an exemplary algorithm used for the elevated prothrombin time (Level II) control is:

Equation 1, 2, and 3: % fluorescence (% pixels on)=100*[0.007*Reaction time−0.6]

The decision tree is the same as the Level I control shown previously. This produces a delayed, lower slope, linear curve more typical of that of a normal Level II sample reaction.

A typical temperature verification algorithm is as follows. To verify that the meter's optical stage is being maintained at the proper temperature, the thermocouple on the electronic verification device periodically (every second) performs a temperature measurement. The results from each temperature are converted into degrees C. if necessary. The degree of deviation of the measured temperature from the ideal temperature is used as input into a temperature correction algorithm. This temperature correction algorithm advances or retards the schedule of pixel switching on the optical shutter in such a way as to mimic the response of a normal test strip-reagent reaction reacting at a deviant temperature. For a prothrombin time reaction, previous work (Daka et al., *Journal of Investigative Surgery* 4: 279–290; 1991), has shown that the optimal reaction temperature for a prothrombin time test is at a reaction time minima, and deviations from this ideal temperature, either positive or negative, prolong the prothrombin time value.

In a normal reagent reaction, the effects of temperature are cumulative. That is, a reaction held at the proper temperature for 95% of the reaction will be only mildly affected if the temperature is slightly deviant during 5% of the reaction. For an exemplary prothrombin time reaction, the effects of non-ideal temperature (either positive or negative) is to slow down the reaction (the ideal temperature is at a reaction time minima). Our own work, as well as the work of Daka et. al., has shown that for the prothrombin time verification device discussed by example here, the effects of non-ideal temperatures on the prothrombin time reaction can be approximated by the equation:

Fluorescence(Time,Temp)=Fluorescence(Time−(a*
(Temperature Deviation)2), where "a" is an experimentally determined coefficient (here taken to be 0.1) used to bring the validation device's temperature variation in line with those of an actual reagent test strip.

The verification device reaction profile, described by the Level I and II equations above, can be temperature compensated to match a normal reagent reaction profile, reacting at a deviant temperature, by subtracting a factor proportional to the time weighted temperature deviation average from the % fluorescence calculation at each relevant time point. This delays the onset of fluorescent development. Higher order polynomial fits, or other temperature compensation functions, can also be used for these purposes.

The meter's microcontroller takes a series of fluorescence readings as for a normal test strip, and interprets the result according to its normal test strip algorithm., Previous work (U.S. Pat. No. 4,418,141 and the Zweig et. al., supra), has shown that for the prothrombin time example illustrated here, the prothrombin time (PT) time correlates linearly with the time at which the normalized fluorescence reaction profile first exceeds 10% of its maximum value (Time 10%). Thus by shifting the time at which the verification device reaction profile first exceeds 10% of its maximum value; the temperature compensation algorithm will cause a corresponding shift in the prothrombin time value reported by the meter after reading the verification device.

FIG. 3 depicts the verification devices' fluorescence profiles reacting according to the Level I and Level II algorithm at a simulated optimal temperature of 37° C., and at an aberrant lower temperature. FIG. 4 shows graphically how the verification device's temperature correction algorithm delays the initial onset of the fluorescent signal (Time 10%) for meters operating at aberrant temperatures.

If the meter is working properly, the answer displayed will be within the expected parameters. If the is fluorescence detector is working improperly, the meter's internal error detection mechanisms will detect a problem (no signal or erratic signal) and display an error code. If the meter's stage is at the incorrect temperature, the deviant pattern of pixel switching on the electronic strip emulator causes the meter to output an answer outside of the expected parameters. The user can either be instructed to not use the system when this happens, and or the meter can itself examine the results, and automatically lock itself into a "safe" mode to prevent outputting an erroneous answer when a real sample is used.

EXPERIMENTAL EXAMPLES

The device constructed according to the preferred embodiment disclosed above was constructed. A fluorescent backing was provided by first mixing 50 mg/ml of Rhodamine-123 in 10 ml of isopropyl alcohol solution, to produce a 5 mg/ml Rhodamine-123 solution. This was mixed in a 1:3 ratio with "Clear Gloss" acrylic finish (lot 404100, Floquil-Pollt S Color Corp., Amsterdam N.Y.) The Rhodamine dye mixed evenly with this acrylic, paint. 10 microliters of this acrylic paint-dye mix was then applied to the back of a Polytronics liquid crystal shutter, and allowed to air dry. When dry, the paint formed a clear durable finish encapsulating the Rhodamine-dye. After drying, the back of the liquid crystal shutter was further coated with black epoxy, forming a more durable, and light opaque fluorescence backing.

The verification device was then programmed as described above for the preferred embodiment, and tested in a prototype Avocet PT-1000 prothrombin time instrument. The instrument responded to the verification device as it would to a normal test strip reacting with sample, and produced appropriate Level I (normal prothrombin time) and appropriate Level II (prolonged prothrombin time) answers.

All references (including appendices, books, articles, papers, patents, and patent applications) cited herein are hereby expressly incorporated by reference in their entirety for all purposes.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A reference device useful for verification of a clinical analytical system having an optical detection apparatus, the reference device comprising:
   an optical shutter;
   an opaque optical reference comprising a fluorescent target with a fluorescent compound incorporated into a support matrix so that any fluorescent intensity of light detected by the system varies as a function of the state of the optical shutter;
   means for controlling the percent exposure of the optical reference to the optical detection apparatus;
   optionally, a means to monitor the temperature of a reaction stage of the clinical analytical system; and
   an algorithm or method that controls the rate at which the optical reference is selectively revealed to the optical detection apparatus, said algorithm or method being selected as to simulate the reaction rates of one or more levels of clinical analytes reacting with a test reagent.

2. The reference device of claim 1, wherein the optical shutter comprises a fluorescent backing on one side of the optical shutter.

3. The reference device of claim 1, wherein the opaque optical reference comprises a fluorescent or luminescent reagent test strip.

4. The reference device of claim 1, wherein the device provides a means to monitor a reagent present sensor and/or a blood present sensor, wherein a stimulus to the sensors is provided to signal readiness of a meter for testing a clinical sample.

5. The reference device of claim 1, wherein the clinical analytical system is an assay system.

6. The reference device of claim 1, wherein the reference device is selected from the group consisting of test strip emulator, a control test simulator, and an electronically controlled optical reference device.

7. The reference device of claim 1, wherein the clinical analytes are enzymatic.

* * * * *